(12) United States Patent
LeVert et al.

(10) Patent No.: US 6,353,656 B1
(45) Date of Patent: Mar. 5, 2002

(54) RADIOISOTOPE BASED X-RAY RESIDUAL STRESS ANALYSIS APPARATUS

(75) Inventors: Francis E. LeVert, Knoxille; David S. Krafsur; E. Beth Pardue, both of Lenoir City; V. Carol Bailey, Knoxville, all of TN (US)

(73) Assignee: Technology for Energy Corporation, Knoxville, TN (US)

( * ) Notice: Subject to any disclaimer, the term of this patent is extended or adjusted under 35 U.S.C. 154(b) by 0 days.

(21) Appl. No.: 09/359,547

(22) Filed: Jul. 22, 1999

Related U.S. Application Data
(60) Provisional application No. 60/093,999, filed on Jul. 24, 1998.

(51) Int. Cl.$^7$ ................................................ G01N 23/20
(52) U.S. Cl. ............................ 378/72; 378/70; 378/71; 378/76
(58) Field of Search .................. 378/70, 71, 72, 378/76

(56) References Cited

U.S. PATENT DOCUMENTS

| | | | |
|---|---|---|---|
| 4,095,103 A | | 6/1978 | Cohen et al. |
| 4,489,425 A | * | 12/1984 | Borgonovi ................ 378/72 |
| 4,561,062 A | * | 12/1985 | Mitchell .................. 702/40 |
| 4,686,631 A | * | 8/1987 | Ruud ...................... 702/42 |
| 5,125,016 A | | 6/1992 | Korhonen et al. |
| 5,148,458 A | * | 9/1992 | Ruud ...................... 378/72 |
| 5,414,747 A | * | 5/1995 | Ruud et al. .............. 378/73 |
| 5,729,587 A | * | 3/1998 | Betz ...................... 378/198 |
| 5,828,724 A | * | 10/1998 | Kurtz ..................... 378/70 |
| 5,848,122 A | * | 12/1998 | Kurtz ..................... 378/80 |
| 6,058,160 A | * | 5/2000 | Kurtz ..................... 378/70 |

OTHER PUBLICATIONS

B.D. Cullity. Elements of X–Ray Diffraction, second edition (Reading, MA: Addison–Wesley, 1978), p. 286 and 447–451.*
B.D. Cullity. Elements of X–Ray Diffraction, second edition (Reading, MA: Addison–Wesley, 1978), p. 178, 204–207, 213–217.*
K.H. Ansell and E.G. Hall—"Recent Developments of Low Energy Photon Sources" Applications of Low Energy X and Gamma Rays, Gordon and Breach, 1970.

(List continued on next page.)

*Primary Examiner*—Robert H. Kim
*Assistant Examiner*—Allen C. Ho
(74) *Attorney, Agent, or Firm*—Pitts & Brittian, P.C.

(57) ABSTRACT

A radioisotope based x-ray residual stress analysis apparatus having a shielded, monoenergetic radioisotopic source to emit x rays for measurement of the stress state of a polycrystalline material. The isotropic source is selected from spontaneously emissive radioisotopes emitting photons in the 5–100 keV energy range. The emissions of the source assembly are measured using either a conventional, solid-state, position sensitive detector or a gas filled position sensitive proportional counter (PSPC). In addition to normal residual stress analysis, the use of a PSPC allows the identification of characteristic photons emitted by particular isotopes to identify trace elements within a sample. As a result of the minimal shielding required for the source assembly and the small size of the isotropic source, the x-ray residual stress analysis apparatus of the present invention is uniquely suited to be configured with an area detector. Finally, the present invention is designed to be powered by commercially available dc batteries allowing residual stress analysis to be performed in remote locations, such as bridges and deserts, where power supplies are not readily available.

2 Claims, 8 Drawing Sheets

OTHER PUBLICATIONS

F.E. LeVVert and E. Helminski—"Literature Review and Commercial Source Evaluation of Americium–241", ORO–4333–1, 1973.

J.F. Cameron—"Portable, Laboratory and On–line Measurements of Coating Thickness using Radioisotope X–Ray Fluorescence Techniques".

W.S. Toothacker and L.E. Preuss—"Radioisotopes as Zero Power Sources of X–Rays for X–Ray Diffraction Analysis" Edsel B. Ford Institute for Medical Research, Detroit, Michigan 48202.

I.C. Noyan and J.B. Cohen—"Residual Stress, Measurement by Diffraction and Interpretation", Handbook of Measuring Residual Stress, Springer–Verlag.

* cited by examiner

RADIOISOTOPE BASED X-RAY RESIDUAL STRESS ANALYSIS APPARATUS

CROSS-REFERENCE TO RELATED APPLICATIONS

This Application claims the benefit of U.S. Provisional Application No. 60/093,999, filed Jul. 24, 1998.

STATEMENT REGARDING FEDERALLY SPONSORED RESEARCH OR DEVELOPMENT

Not Applicable

BACKGROUND OF THE INVENTION

1. Field of Invention

This invention relates to an apparatus for use in x-ray residual stress analysis. More specifically, this invention relates to an x-ray residual stress analysis apparatus having a radioisotope for generating x-ray emissions.

2. Description of the Related Art

X-ray residual stress analysis, a subset of x-ray diffraction, is a well-known technique for measuring stress in crystalline materials. A detailed discussion of the technique and the various apparatuses that employ this technique for the non-destructive examination of materials can be found in a text by I. C. Noyan and J. B. Cohen, entitled *Residual Stress: Measurements by Diffraction and Interpretation*, published by Springer-Verlag in 1987.

All of the x-ray residual stress analysis devices discussed by Noyan and Cohen utilize an x-ray tube composed of an anode and a cathode where electrons emitted by the cathode are accelerated at high velocities into the anode. The interaction of the electrons with the anode produces a continuum of bremsstrahlung photons with energies distributed over a wide energy range and a photon with a specific energy that is characteristic of the anode (target) material. Thus, the energy spectrum of an x-ray tube has a characteristic line superimposed on a bremsstrahlung background. For the energy spectrum to be useful, the bremsstrahlung background must be removed or reduced either electronically or by using mechanical filters.

Typically, the characteristic x-ray energies employed in residual stress vary between 5.4 and 17 keV. Elemental radioisotopes emit photons originating in the nucleus or in the atomic shell surrounding the nucleus having energies within this energy range. However, x-ray energies in excess of 10 keV present special detection problems for silicon-based solid state detectors. As photon energy increases, the stopping power of the silicon in a solid state photodiode array declines. More photons simply pass through the active volume of the silicon undetected. The use of a phosphor material as a scintillator optically coupled to a photodetector permits efficient measurement at higher photon energies. Cesium Iodide(Thallium) (CsI(Tl)) and Gadolinium Oxysulfide ($GdO_2 S$) are two such phosphor materials shown to have high sensitivities over a range of wavelengths extending from approximately 10 keV to approximately 100 keV.

The efficiency of a photodiode array (PDA) to directly detect x rays compared to a phosphor screen coated PDA can be examined using a few simple calculation. In a silicon-based PDA, the number of electron hole pairs per x ray directly produced by a 10 keV x ray is:

$$\frac{10000 \text{ eV}}{3.65 \frac{\text{eV}}{\text{ion pair}}} = 2740 \frac{\text{electron hole pairs}}{\text{x ray}} \quad (1)$$

The results in Equation 1 assume that the total energy of the x ray is absorbed in the active region of the silicon.

According to a paper published in 1991 by Valentine et al., entitled "Charge Calibration of Systems with CsI(Tl), a Photodiode and a Charge Sensitive Preamplifier," in Nuclear Instrumentation Methods, 1991, a CsI(Tl) coated PDA will yield an average of 47,900 electron hole (e. h.) pairs per MeV of photon energy for CsI in the temperature range of −15° to 40° C. The decay constant for CsI is 6 $\mu$sec. This is important only for high x-ray interaction rates within the CsI. For 10 keV x rays interacting with the CsI, this produces:

$$47,900 \frac{\text{e.h. pairs}}{\text{MeV}} \cdot 0.010 \text{ eV} = 479 \frac{\text{e.h. pairs}}{\text{interaction}} \quad (2)$$

In both Equations 1 and 2, the total amount of charge deposited in the photodiode will be determined by the flux of the x-ray beam. For example, if it is assumed that the event rate within a photodiode is one x ray per second, then the continuous current produced in the photodiode would be:

$$2740 \frac{\text{e.h. pairs}}{\text{x ray}} \cdot 1 \frac{\text{x ray}}{\text{sec.}} \cdot 1.6 \times 10^{-19} \text{C} = 0.00043 \text{ pA} \quad (3)$$

For the CsI photodetector combination and an assumed interaction rate of one x ray per second, the decay time (6 $\mu$sec) of the phosphor is much shorter than the event rate within the photodetector; hence, there are no overlapping pulses. Therefore, each photon generated within the scintillator and interacting with the photodiode will be detected. This yields a peak current per x-ray event of:

$$479 \frac{\text{e. h. pairs}}{\text{event}} \cdot \frac{1}{6 \text{ ms}} \cdot 1 \times 10^6 \frac{\text{ms}}{\text{s}} \cdot 1.6 \times 10^{-19} \text{C} = 0.0127 \frac{\text{pA}}{\text{event}} \quad (4)$$

For a 5.4 keV x ray, the current produced in a bare and a CsI coated photodetector are estimated to be 0.235 and 6.5 pA/event, respectively.

While systems that utilize phosphor screens attached to a fiber-optic bundle optically coupled to an array of photodetectors are commercially available, it is desirable to employ such a phosphor screen/detector combination with an x-ray residual stress analysis device incorporating an isotropic source.

Other x-ray diffraction apparatuses have been developed for use in x-ray diffraction studies using conventional x-ray tubes. Typical of the art are those devices disclosed in the following U.S. Patents:

| U.S. Pat. No. | Inventor(s) | Issue Date |
|---|---|---|
| 5,125,016 | Korhonen, M. et al. | Jun. 23, 1992 |
| 4,095,103 | Cohen, J. et al. | Jun. 13, 1978 |

U.S. Pat. Nos. 5,125,016 and 4,095,103 both employ a conventional x-ray tube as the emission source for the x rays used in diffraction studies. Both the '016 and the '103 patents disclose the use of x-ray tubes in conjunction with one or two position sensitive detectors for use in single or multiple exposure x-ray diffraction studies. However, conventional x-ray tubes are too large to be practical when developing a miniaturized battery powered x-ray residual stress apparatus.

Sources of monoenergetic photons have been used for many years in fluorescence analysis of materials. Typical source designs may be found in an article by K. H. Ansell and E. G. Hall, entitled "Recent Developments of Low Energy Photon Sources," published in the text *Applications of Low Energy X and Gamma Rays*, edited by Ziegler, and published by Gordon and Breach in 1970 and a publication by F. E. LeVert and E. Helminski, entitled "Literature Review and Commercial Source Evaluation of Americium-241," ORO-4333-1, 1973. In these cases, the radioisotope may be a direct emitter of x rays (e.g., the electron capture process in Fe-55 leading to the 5.8 keV Mn x ray) or the x rays may be generated indirectly by using a monoenergetic source of photons to excite characteristic x rays in various pure element targets. To be of analytic use, the resulting direct or indirect x-ray radiation must be highly monoenergetic with negligible background contributions.

A paper presented by William S. Toothacker and Luther E. Preuss entitled "Radioisotopes as Zero Power Sources of X-rays for X-ray Diffraction Analysis," published in Nucleonics in Aerospace by the Instrument Society of America, 1968, discussed the use of an isotropic source in x-ray diffraction. For purposes of this application, it is important to distinguish between x-ray diffraction and x-ray residual stress analysis. X-ray diffraction is the study of the structure of crystals and complex molecules through the diffractive properties of these bodies. Toothacker taught the use of a radioisotope as an x-ray source for the study of the structure and composition of matter. Given the definition of x-ray diffraction accepted by those persons skilled in the art, Toothacker does not make obvious the use of a radioisotope as a sealed x-ray source for residual stress analysis.

Residual stress analysis is different from x-ray diffraction in that x-ray diffraction is used to identify the composition of matter while residual stress analysis is used to determine the state of a material. Specifically, residual stress measurements are normally performed at $2\theta$ angles greater than 140 degrees whereas x-ray diffraction pattern measurements are normally performed in the forward reflected region, i.e., at $2\theta$ angles less than 90 degrees. As the $2\theta$ angle increases, the x-ray fluence of the diffracted beam decreases. Therefore, it is necessary for the detector and the emitter to be placed in closer proximity in order to maintain an adequate event rate in the detector. Accordingly, the detectors used for residual stress measurement must be more compact than those typically used for standard or powder x-ray diffraction. Toothacker discussed the difficulties encountered when using a sealed source with a detector positioned at a low back reflection angle. The intensity of the reflected beam measured at low back reflection angles is typically greater than the measured intensity at high back reflection angles. As most residual stress measurements are made at high back reflection angles, it is not obvious from the teaching of Toothacker that an isotropic source would be suitable for the low intensity measurements common in residual stress analysis.

That Toothacker does not make obvious the applicability of an isotropic source in residual stress analysis is further emphasized by the size limitations on detectors inherent in residual stress analysis. In order to obtain measurements at the requisite high back reflection angles, the source and the detector must be placed in closer proximity than in conventional x-ray diffraction studies. Accordingly, it is necessary to minimize the size of the detector, including the active detection area, to achieve the desired proximity. However, limitations in conventional electronics present special problems in developing the compact detectors necessary for efficient residual stress analysis. A similar reduction is desired in the size of the x-ray emitter requiring the use of a smaller source. While an isotropic source presents the possibility of smaller sources, the practical problems associated with the use of isotropic sources have prevented its use. Such problems include the low intensity and the lack of resolution associated with the low intensity, which were noted by Toothacker. Accordingly, in light of the difficulties encountered by Toothacker with a large proportional counter and the inherent difficulty in producing smaller detectors, it is not obvious that a position sensitive detector having a smaller active detection area would be effective.

Because of the differences between x-ray diffraction analysis and residual stress analysis, Toothacker does not make obvious to one of ordinary skill in the area of residual stress analysis that a sealed source would have either the intensity required to yield the resolution needed for precise determination of the angular location of the peak of a diffracted x-ray beam or the intensity required for the measurement of residual stress in a specimen.

Accordingly, there is a need for an x-ray residual stress analysis apparatus employing an x-ray source having a size smaller than that which is possible using conventional x-ray tubes. Additionally, there is a need for an x-ray residual stress analysis apparatus having a source which does not generate excessive background noise to the measurements. Further, there is a need for an x-ray residual stress analysis apparatus which is capable of simultaneous multiple angular exposures to reduce measurement times. Still further, there is a need for an x-ray residual stress analysis apparatus which is capable of efficient residual stress analysis when the intensity of the primary and reflected beams from an x-ray source and a target material, respectively, are low. Finally, there is a need for a practical x-ray residual stress analysis apparatus employing an area detector.

Therefore, it is an object of the present invention to provide an x-ray residual stress analysis apparatus which employs an x-ray source comprising a radioisotope that can be selectively exposed to a target material.

Another object of the present invention is to provide an x-ray residual stress analysis apparatus having an x-ray source producing essentially a monoenergetic x-ray beam.

Yet another object of the present invention is to provide an x-ray residual stress analysis apparatus capable of taking simultaneous exposures covering multiple angles.

An additional object of the present invention is to provide an x-ray residual stress analysis apparatus having a detector which is efficient at photon energies greater than 10 keV.

A further object of the present invention is to provide an x-ray residual stress analysis apparatus that does not require an external power source allowing it to be used in remote locations.

BRIEF SUMMARY OF THE INVENTION

A radioisotope based x-ray residual stress analysis apparatus using a shielded, monoenergetic radioisotope, or isotropic, source to emit x rays for measurement of the stress state of a polycrystalline material. The isotropic source is selected from spontaneously emissive radioisotopes emitting photons in the five to one hundred (5–100) keV energy range. The source assembly may be sealed or unsealed. The source may be a direct emitter of monoenergetic x rays or it may be selected from a class of indirect x-ray emitters where a source of radiation is used to produce the characteristic x ray of an integral target material.

The isotropic emissions are focused into a beam directed at a point on the sample. The sample diffracts the emitted beam into a diffraction cone, represented by diffracted beams. The diffracted beams are detected by at least one position sensitive detector, either directly or indirectly.

The source assembly and position sensitive detector are connected in a manner that allows mechanical variation of the angle, ξ, between the two position sensitive detectors or the angle, β, between the source assembly and the sample perpendicular. When the diffracted beam strikes the position sensitive detector, an electrical charge proportional to the x-ray energy absorbed in each of the photodiodes is created and stored therein. This charge is subsequently conditioned and outputted as a voltage signal corresponding to a position within the photodiode array. The position sensitive detectors are electrically coupled to conventional signal conditioning electronics which amplify and otherwise condition the signal. The conditioned signal is transferred to an analysis and storage device.

As a result of the minimal shielding required for the source and the small size of the isotropic source, the x-ray residual stress analysis apparatus of the present invention is uniquely suited to be configured with an area detector.

The position sensitive photodiode array(s) may be replaced with gas filled position sensitive proportional counters (PSPCs). In addition to normal residual stress analysis, the use of a PSPC allows the identification of characteristic photons emitted by particular isotopes through the discrimination of output pulses having an amplitude proportional to the energy of incident photons. When conditioned signals from the PSPC are analyzed by an analysis unit, these secondary x-ray fluorescence (XRF) photons can be used to identify trace elements within a sample.

Finally, the present invention is designed to be powered by commercially available dc batteries allowing residual stress analysis to be performed in remote locations, such as bridges and deserts, where other sources of electronic power are not readily available.

The present invention offers the capability to make non-destructive measurements of the stress state of machinery actually operating in the field under normal operating conditions. One such area where frequent field measurements are desirable is the railroad industry. The rails of railroad tracks and the wheels of railroad cars are exposed to high stresses due to increased traffic, speed, and axle loads. Using the portable, radioisotope-based residual stress analysis device of the present invention, it is possible to go to remote locations and rapidly measure the in situ longitudinal stresses in rails and the residual compressive stresses in wheels.

BRIEF DESCRIPTION OF THE SEVERAL VIEWS OF THE DRAWINGS

The above mentioned features of the invention will become more clearly understood from the following detailed description of the invention read together with the drawings in which:

FIG. 4b illustrates a bottom plan view of the x-ray residual stress analysis apparatus of FIG. 4a;

FIG. 5b illustrates a bottom plan view of the planar area detector of the x-ray residual stress analysis apparatus of FIG. 5a;

DETAILED DESCRIPTION OF THE INVENTION

A radioisotope based x-ray residual stress analysis apparatus incorporating various features of the present invention is illustrated generally at 10 in the figures. The x-ray residual stress analysis apparatus uses a radioisotope source to emit x rays for measurement of the stress state of a polycrystalline material.

Figure 1:
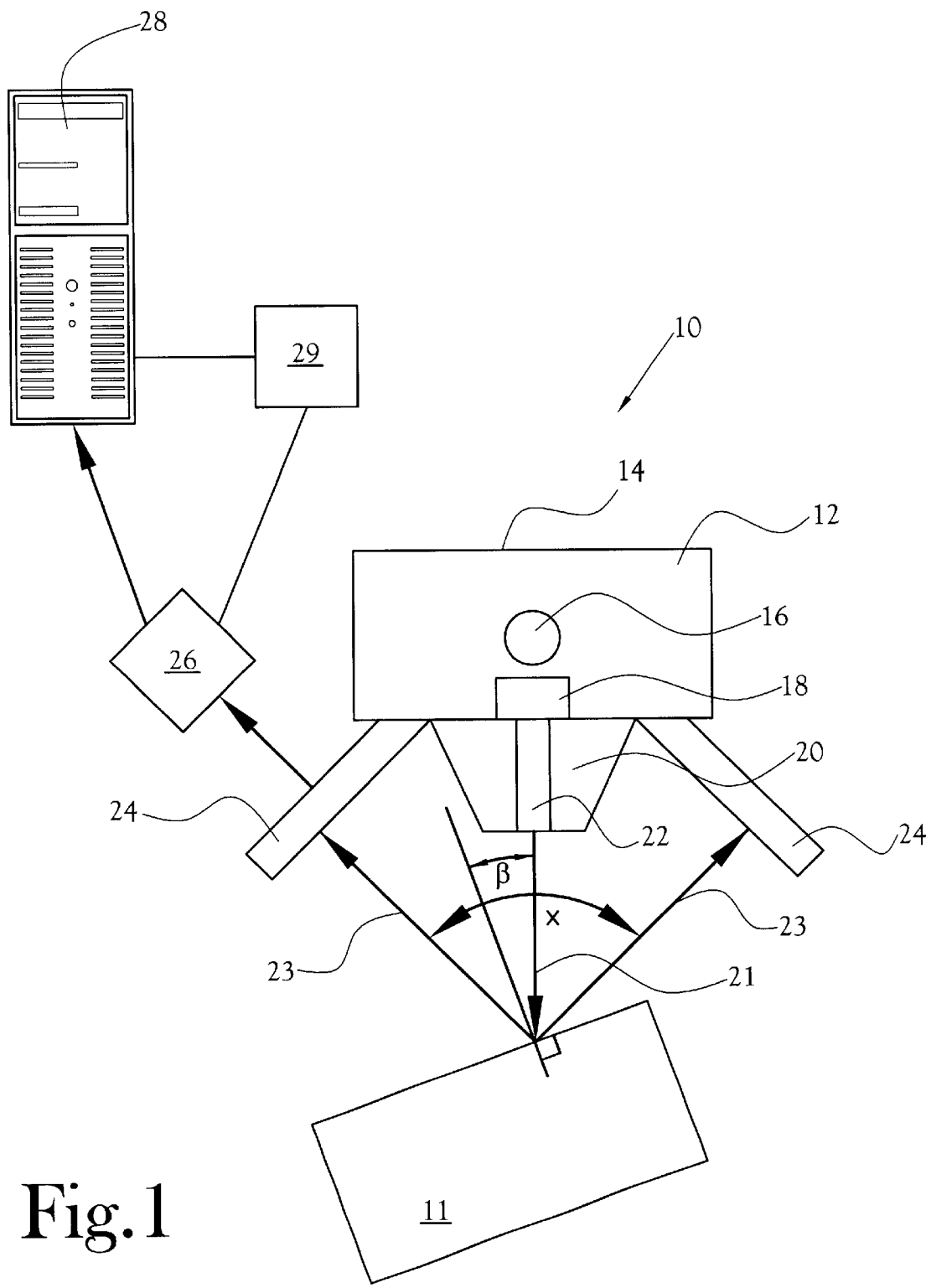
FIG. 1 illustrates a schematic view of an x-ray residual stress analysis apparatus incorporating various features of the present invention.

FIG. 1 illustrates a schematic diagram of the residual stress analysis apparatus 10. The source assembly 12 comprises a source shield 14 which houses a radiation source 16 and a shutter 18. In the illustrated embodiment, the radiation source 16 is a monoenergetic radioisotope, or isotropic source. Those skilled in the art will recognize that a x-ray tube can be used instead of the isotropic source without departing from the scope and spirit of the present invention. The isotropic source 16 is selected from spontaneously emissive radioisotopes emitting photons in the 5–100 keV energy range. The source shield 14 is fabricated from a suitable shielding material having sufficient thickness such that x rays escape only in a selected direction through an aperture (not shown) provided for that purpose. The shutter 18 permits exposure of the isotropic source 16 to a sample 11. One skilled in the art will recognize that the source assembly 12 may be sealed or unsealed and that the isotropic source 16 may be a direct emitter of monoenergetic x rays or it may be selected from a class of indirect x-ray emitters where a source of radiation is used to produce the characteristic x ray of an integral target material.

The sample 11 is a polycrystalline material on which the stress state is to be measured. A collimator 20 collimates the isotropic emissions into a beam through collimation path 22 and directs the collimated beam 21 to a point on the sample 11. The sample 11 diffracts the collimated beam 21 into a diffraction cone, represented by diffracted beams 23. The diffracted beams 23 strike at least one position sensitive detector 24, such as a photodiode array. In the illustrated embodiment, each position sensitive detector 24 is a linear photodiode array. One skilled in the art will recognize that when the apparatus 10 is used in single exposure mode, two position sensitive detectors 24 are required.

Figure 2:
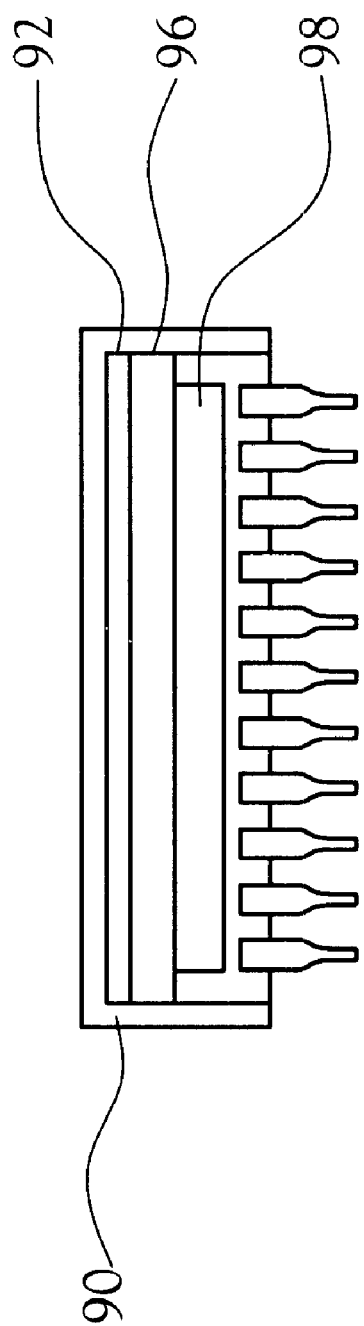
FIG. 2 illustrates a schematic view of a phosphor-coated position sensitive detector for use with the present invention.

In an alternate embodiment, the position sensitive detector 25 is a phosphor-coated detector array known to those persons skilled in the art and illustrated in FIG. 2. A housing 90 encapsulates substantially all of the phosphor-coated detector array 25. In the preferred embodiment, the housing 90 is aluminum. The phosphor-coated detector array 25 contains a phosphor layer 92 in optical communication with a photodiode array 98 via an optical coupling 96. A layer of optical coupling grease is applied to improve the communication between the optical coupling 96 and the photodiode array 98.

Returning now to FIG. 1, the source assembly 12 and position sensitive detector 24 are connected in a manner that allows mechanical variation of the angle, ξ, between the two position sensitive detectors 24 or the angle, β, between the source assembly 12 and the sample perpendicular. When the diffracted beam 23 strikes the position sensitive detector 24, an electrical charge proportional to the x-ray energy absorbed in each of the photodiodes is created and stored therein. This charge is subsequently conditioned and outputted as a voltage signal corresponding to a position within the photodiode array.

The position sensitive detectors 24 are electrically coupled to conventional signal conditioning electronics 26 which amplify and otherwise condition the signal. The conditioned signal is transferred to an analysis and storage device 28, such as a computer. Both the signal conditioning electronics 26 and the analysis and storage device 28 are powered by a power source 29. The computer 28 computes and displays the stress state of the sample. In the preferred embodiment, the power source 29 is a conventional dc battery with the computer 28 selectively energizing the signal conditioning electronics 26 and other power consuming components of the residual stress analysis apparatus 10.

Figure 3:
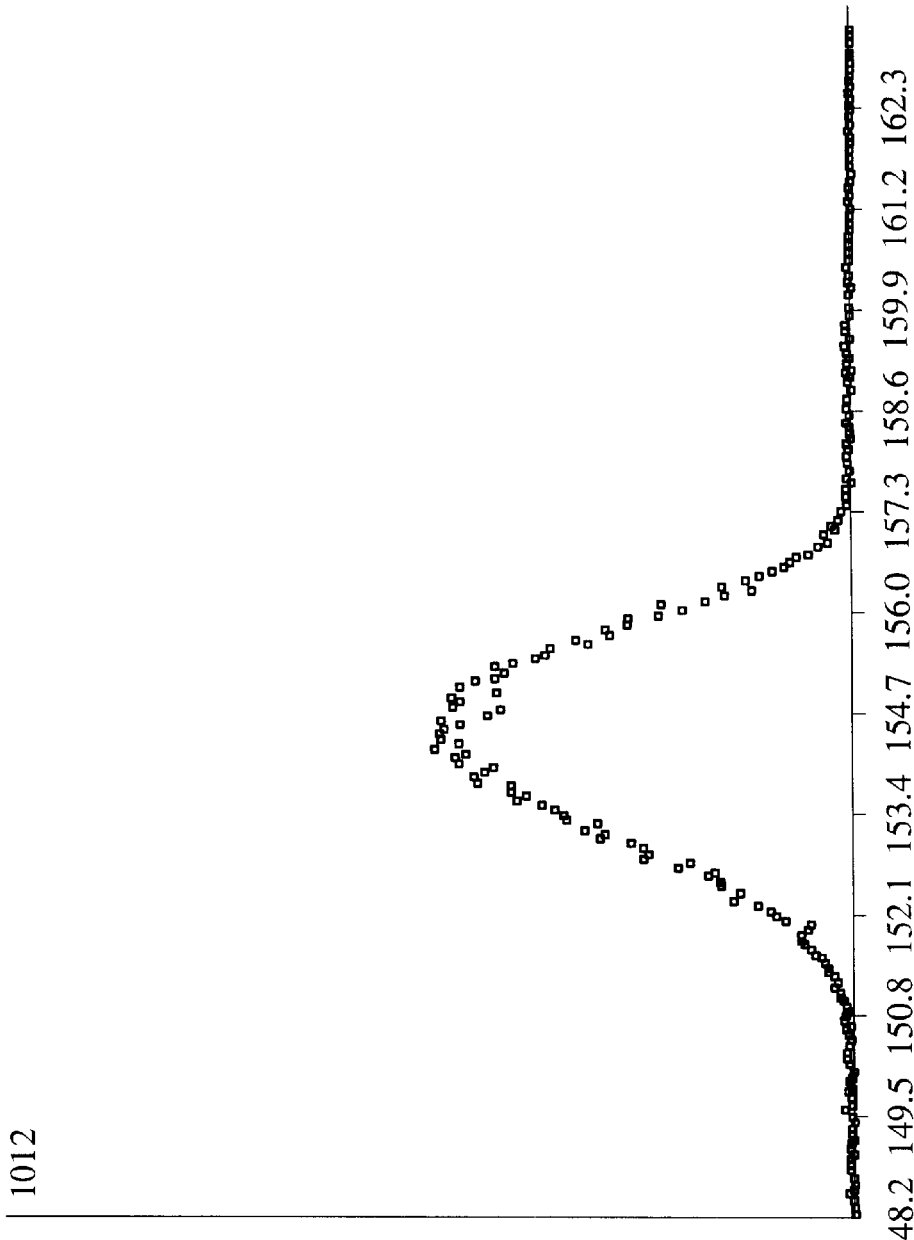
FIG. 3 shows a graphic representation of an x-ray residual stress analysis spectrum obtained from a NIST Austenite in Ferrite Standard, SN 261, using the x-ray residual stress analysis apparatus of the present invention employing a 100 mCi Fe-55 x-ray source.

FIG. 3 shows a diffraction spectrum obtained using a sealed source. Specifically, FIG. 3 shows the spectrum diffracted from a standard sample, NIST Austenite in Ferrite Standard, SN 261, using a 100 mCi Fe-55 isotropic source. One skilled in the art will recognize that the geometry of the source may be any of several shapes, such as a point source, that facilitate the emission and focusing of photons from the source on a selected target area. The source used in the illustrated example is a single disc source. Further, the use of multiple point sources allows multiple angular exposures to be obtained simultaneously.

Figure 4A:
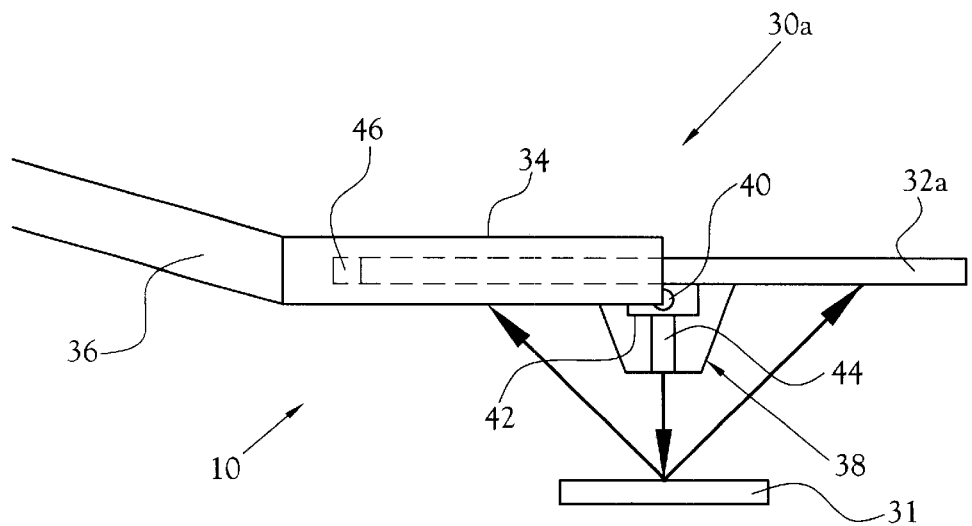
FIG. 4a illustrates a side elevation view of one embodiment of a planar area detector of the x-ray residual stress analysis apparatus of the present invention.
Figure 4B:
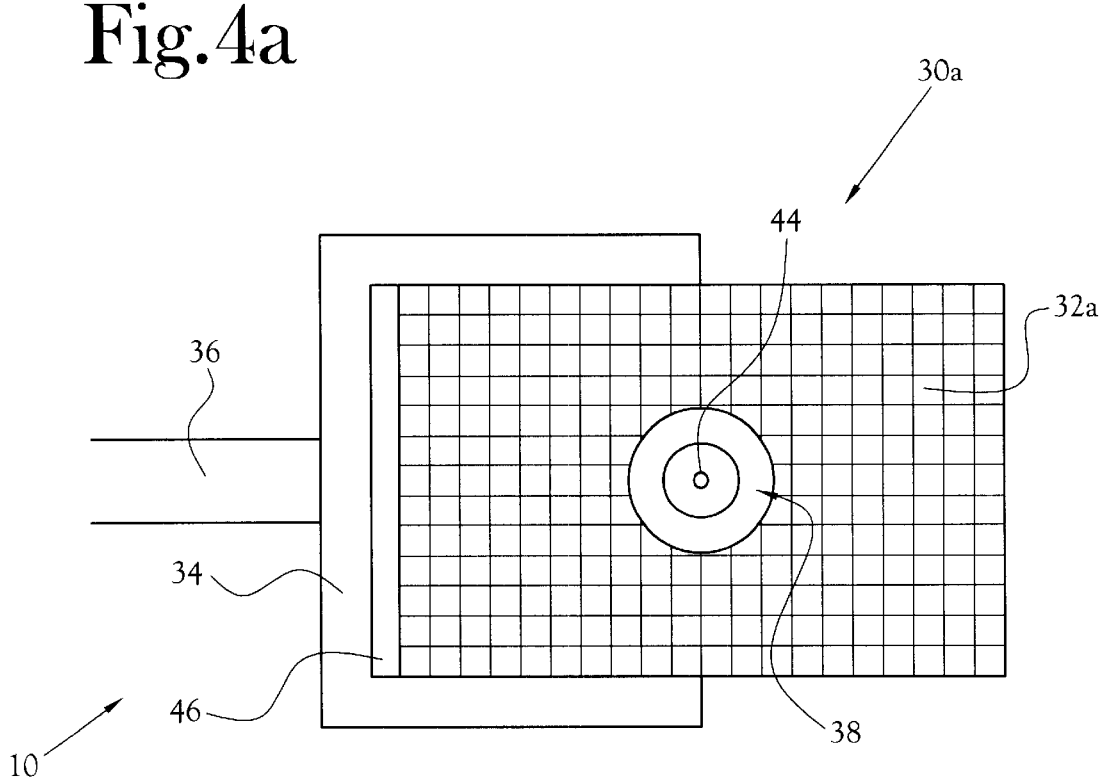

As a result of the minimal shielding required for and the small size of the isotropic source 16, the x-ray residual stress analysis apparatus 10 of the present invention is uniquely suited to be configured with an area detector 30a with the numeric designation being followed by an ascending alphabetic identifier to distinguish unique embodiments in collective FIGS. 4 and 5. FIG. 4a illustrates the radioisotope based x-ray residual stress analysis apparatus 10 of the present invention using one embodiment of an area detector 30a. The area detector 30a includes a planar array of photodetectors 32a, or detector plate, and a source assembly 38. One skilled in the art will recognize that the individual photodetectors can have various arrangements, such as a rectilinear or a circular geometry. In the illustrated embodiment, the source assembly 38 is mounted on the active face of the detector plate 32a. The source assembly 38 includes a source shield 42 for containing the isotropic source 40. The source shield further defines a collimation path 44 for directing the emissions from the isotropic source 40 to a point on the sample 31. The detector plate 32a is secured by a detector holder 34 attached to a scanning arm 36. The scanning arm 36 serves to position the detector plate 32a relative to a sample 31 of a polycrystalline material during residual stress analysis. A prism 46 houses the signal conditioning electronics (not shown). FIG. 4b illustrates the detector plate 32a having the photodetectors arranged in a rectilinear geometry.

Figure 5A:
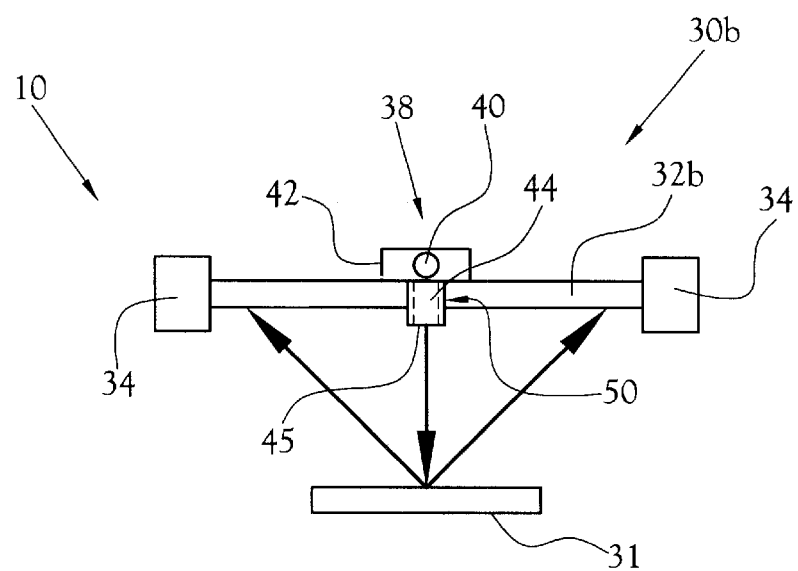
FIG. 5a illustrates a front elevation view of another embodiment of the planar area detector of the x-ray residual stress analysis apparatus of the present invention.
Figure 5B:
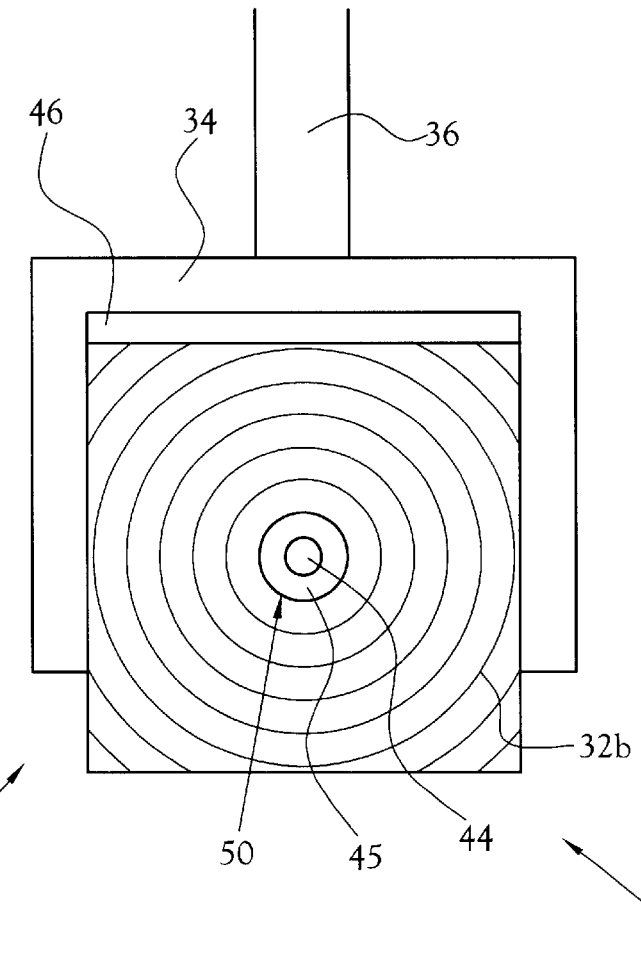

FIG. 5a illustrates the radioisotope based x-ray residual stress analysis apparatus 10 of the present invention using another embodiment of the area detector 30b. In the illustrated embodiment, the individual photodiodes of the area detector 30b are arranged in a circular geometry. Further, the detector plate 32b defines a centrally disposed through opening 50. The through opening 50 is sized to releasably receive the collimated end 45 of a source assembly 38. The source assembly is designed to be removed to facilitate the use of various isotropic sources 40. FIG. 5b illustrates the detector plate 32b with the source assembly received within the through opening 50.

Figure 6:
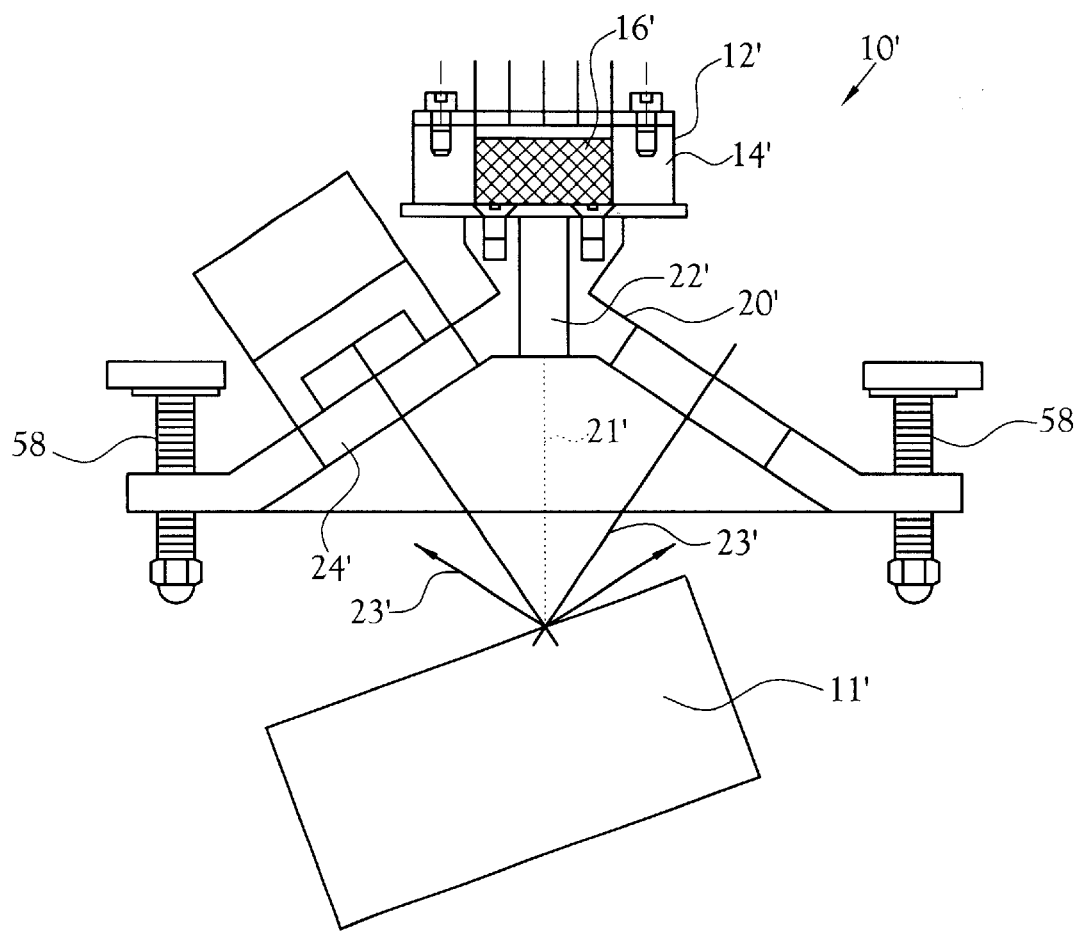
FIG. 6 illustrates a schematic view of an alternative embodiment of the x-ray residual stress analysis apparatus of the present invention.

In an alternate embodiment of the present invention, the standard photodiode array (PDA) or charge coupled device (CCD) position sensitive detectors 24 are replaced with gas filled position sensitive proportional counters (PSPC) 24', as illustrated in FIG. 6. The source assembly 12' is configured to be rotatable to allow the isotropic source 16' to be rotated to a shielded position when not in use. The residual stress analysis apparatus 10' further includes an adjustment device 58 allowing the adjustment of the incident angle of the primary x-ray beam 21' with respect to the target sample 11'.

Figure 7A:
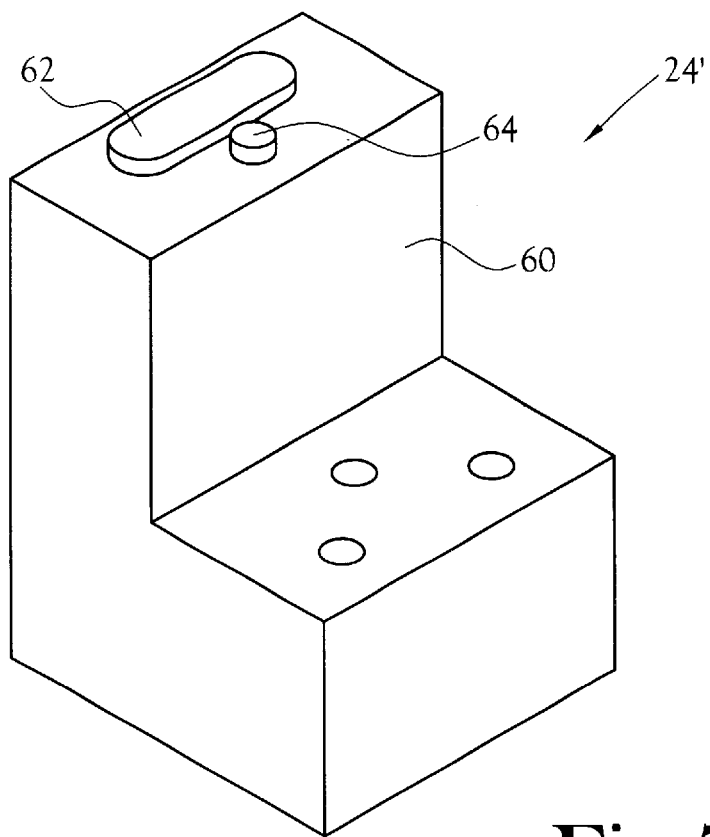
FIG. 7a illustrates a top perspective view of a position sensitive proportional counter (PSPC) used in the embodiment of FIG. 6.
Figure 7B:
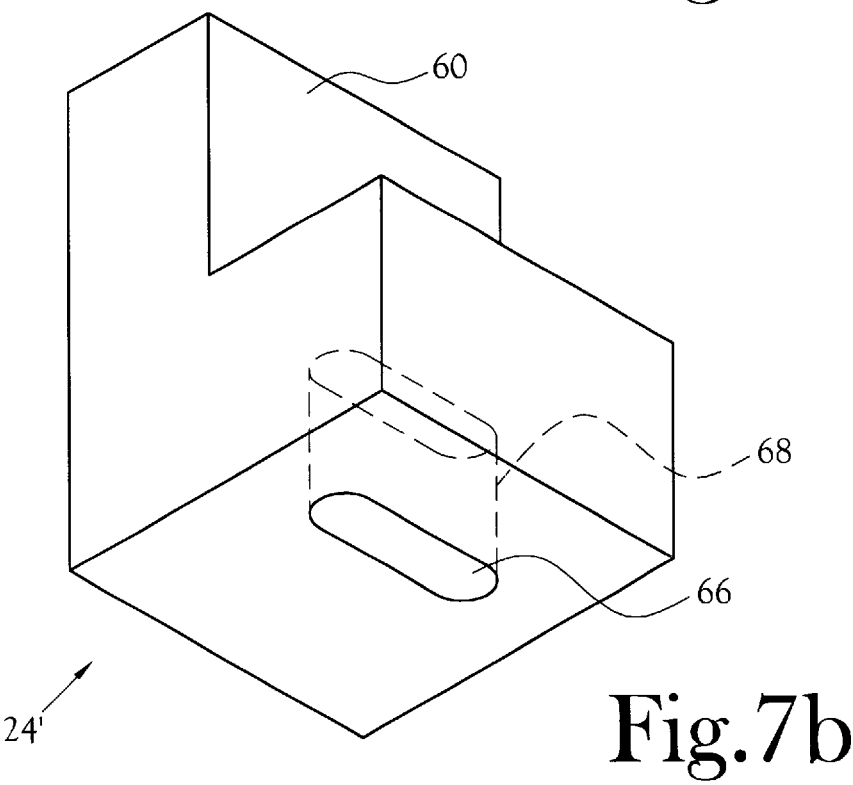
FIG. 7b illustrates a bottom perspective view of the PSPC used in the embodiment of FIG. 6.
Figure 8:
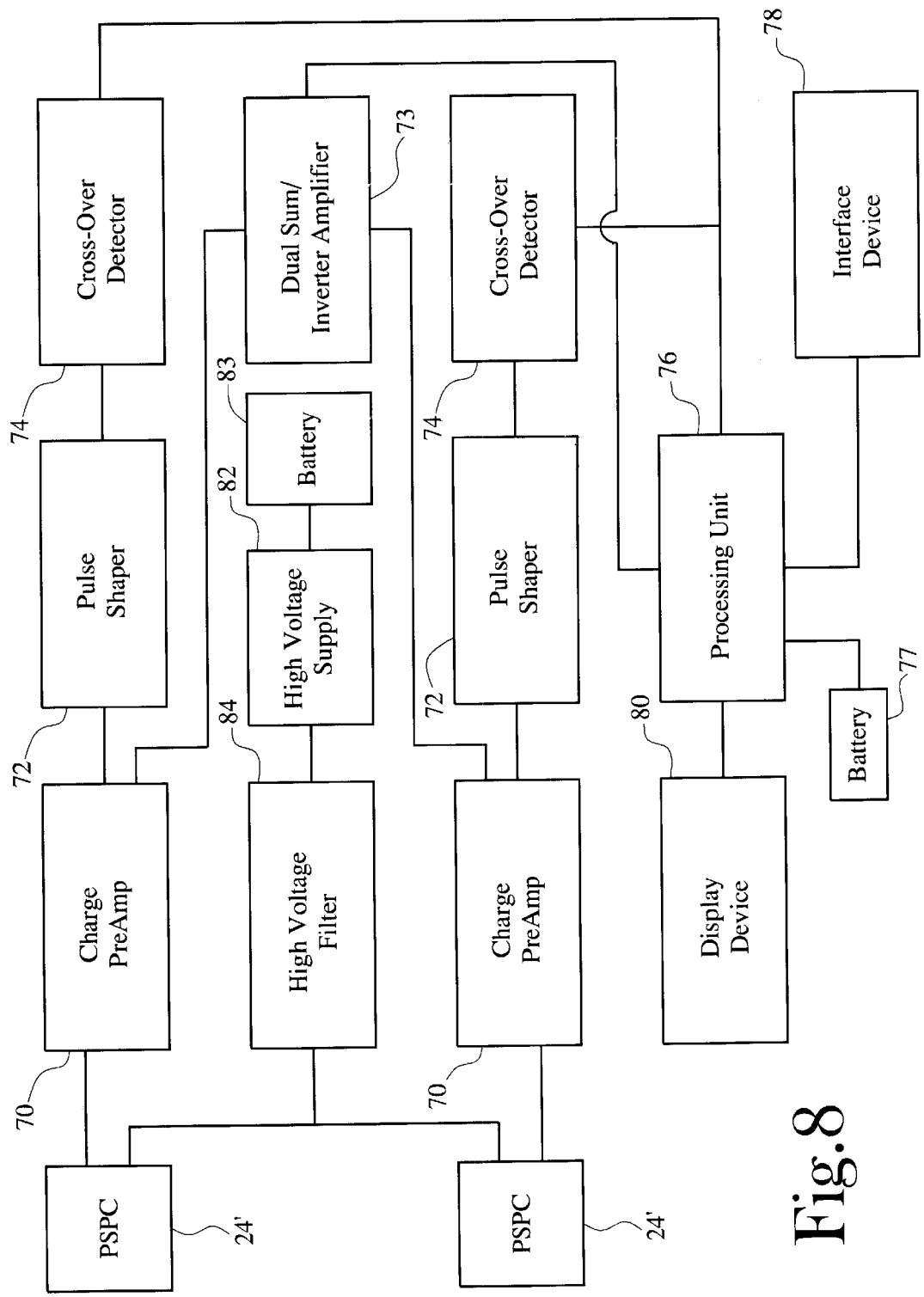
FIG. 8 illustrates a block diagram of the x-ray residual stress analysis apparatus of FIG. 6.

FIGS. 7a and 7b illustrate perspective views from differing angles of the PSPC 24'. The PSPC 24' is depicted as an "L"-shaped housing 60. One skilled in the art will recognize that the housing 60 could take various other forms. Visible in FIG. 7a is a top perspective showing the power signal connector 62 and the high voltage bias connector 64. The bottom perspective view of FIG. 7b illustrates the x-ray transparent window 66 through which the diffracted beams 23' are received. The window 66 covers a volume 68 defined by the "L"-shaped housing 60 and filled with an x-ray sensitive gas. In the illustrated embodiment, the PSPCs 24' are filled with $XeCO_2$. The anode (not shown) of the PSPC 24' has a diameter of approximately between 0.0003 and 0.004 inches and an active length which may vary between 0.25 and 1.5 inches. One skilled in the art will recognize the diameter and the active length of the PSPC anode can vary without interfering with the objects of the present invention. In the preferred embodiment, the anode is assembled using a resistive conductor such as a carbon-coated quartz wire or any other resistive material. The PSPC 24' is designed to respond to x rays with energies in the 4 to 20 keV range.

Disposed within the PSPC housing 60 is the charge-to-voltage conversion and signal conditioning electronics. A charge pre-amplifier 70 amplifies the analog signals generated by x-ray interactions within the active volume of the PSPC 24'. A dual sum inverter 73 combines the output pulses of the charge pre-amplifier 70 to produce a conventional proportional counter pulse for use in generating energy spectra and for elemental identification in fluorescence analysis. A pulse shaper 72 conditions the output pulse of the charge pre-amplifier prior to introduction to a zero-crossing detector 74 used for position decoding and background discrimination. The outputs of the zero-crossing detector 74 and the dual sum inverter 73 are fed into a processing device 76 which analyzes the electrical signals to determine a plurality of diffraction peaks that are used to determine the stress at a point on the sample 11'. The results are displayed on a display device 80 and an interface device 78 allows the operator to control the operation of the processing unit 76. One skilled in the art will recognize that the processing device 76, the interface device 78, and the display device 80 could be embodied in a conventional microcomputer.

Unlike the solid state photodetector arrays 24 of the first embodiment, the PSPCs 24' require the use of a high voltage supply 82 to properly bias the anode and cathode of the PSPC 24' for charge collection after each x-ray interaction within the active volume of the PSPC 24'. The high voltage supply 82 is connected to the PSPCs 24' through a high voltage filter 84. While the required use of a high-voltage supply 82 for charge collection increases the complexity of the apparatus, the use of the PSPC 24' offers both increased x-ray efficiency for x rays of approximately 5 to 10 keV and a much larger equivalent active target area per pixel for x-ray interactions than that of a commercially available PDA of equal active lengths. The high voltage power supply 82 and the signal conditioning electronics are both powered by commercially available dc batteries 77, 83 for use where other sources of electronic power are not readily available.

Additionally, the use of a PSPC 24' provides an additional function not present in x-ray residual stress analysis devices using solid state photodetectors. A PSPC 24' produces output pulses having an amplitude proportional to the energy of incident photons. This allows energy discrimination via electronic signal conditioning and pulse height analysis to reduce background noise and identify characteristic photons emitted by particular isotopes.

In addition to the simple Bragg angle diffraction elastic scattering used by the present invention to measure the stress state of a crystalline sample, other photon interaction processes occur when a photon undergoes interactions within a material. The capability for energy selectivity, which is inherent in the pulse characteristics of the output signals of the PSPC, allows the identification of isotopes in samples. Inelastic photon-specimen interactions in which some energy is lost by the x-ray photon results in secondary signals which contain information about sample atoms. For example, an x ray can ionize a sample atom by removing inner K-shell electrons. The resulting inner shell vacancies are filled by electrons from the outer L-shells of the atom and the difference in energy between the two orbitals is manifested as either secondary x rays or an Auger electron. This phenomenon, which results in the emission of a secondary photon, is known as fluorescence. The energies of the secondary x rays are characteristics of the elements from which they are emitted, and the number of x rays and their energies can be translated into major, minor, and trace element abundances.

When conditioned signals from the PSPC 24' are analyzed by an analysis unit, such as that used in the subject invention, using well-known spectroscopy principles, (see, for example, R. D. Evans, *The Atomic Nucleus*, McGraw-Hill 1955), these secondary x-ray fluorescence (XRF) photons can be used to identify trace elements within a sample.

Finally, the low power requirements of the present invention allow it to be operated by a commercially available dc power source. Such an arrangement permits the x-ray residual stress analysis apparatus to be used in remote locations where external power sources are not readily available. One skilled in the art will recognize that the radioisotopic source could be replaced with a conventional x-ray tube due to the unique power requirements of the present invention allowing a battery-powered x-ray tube based residual stress analysis device to be used in remote locations like its radioisotopic counterpart.

While a preferred embodiment has been shown and described, it will be understood that it is not intended to limit the disclosure, but rather it is intended to cover all modifications and alternate methods falling within the spirit and the scope of the invention as defined in the appended claims.

What is claimed is:

1. An x-ray residual stress analysis apparatus for residual stress analysis of a polycrystalline sample comprising:

a radioisotopic source for emitting monoenergetic x rays, said radioisotopic source selected from the group of spontaneously emissive radioisotopes emitting photons having energies between about 5 keV and about 100 keV;

a source assembly for housing said radioisotopic source;

a collimator configured to operate in conjunction with said source assembly for aligning said monoenergetic x rays into a beam and for directing said beam at a polycrystalline sample which diffracts said beam into a plurality of diffracted beams;

at least one position sensitive detector responsive to said monoenergetic x rays for detecting at least one of said diffracted beams, said at least one position sensitive detector generating an output, said output containing position information about where said diffracted beam struck said at least one position sensitive detector;

a storage device in electrical communication with said at least one position sensitive detector for storing either of said output or said result;

an analysis device in electrical communication with said storage device and said at least one position sensitive detector for analyzing said output as a result, said analysis device selectively energizing power consuming components including at least said storage device;

an interface device in electrical communication with said analysis device and said position sensitive detector for relaying commands from an operator to said analysis device, controlling said position detector, and displaying either of said output or said result, said interface device being selectively energized by said analysis device; and at least one power source in electrical communication with said at least one position sensitive detector, said analysis device, said storage device, and said interface device.

2. An x-ray residual stress analysis apparatus for residual stress analysis of a polycrystalline sample comprising:

an x-ray tube for emitting monoenergetic x rays having photon energies between about 5 keV and about 100 keV;

a collimator configured to operate in conjunction with x-ray tube for aligning said monoenergetic x rays into a beam and for directing said beam at a polycrystalline sample which diffracts said beam into a plurality of diffracted beams;

at least one position sensitive detector responsive to said monoenergetic x rays for detecting at least one of said diffracted beams, said at least one position sensitive detector generating an output, said output containing position information about where said diffracted beam struck said at least one position sensitive detector;

an analysis device in electrical communication with said at least one position sensitive detector for analyzing said output as a result, said analysis device selectively energizing power consuming components including at least said storage device, sad interface device, and said x-ray tube;

a storage device in electrical communication with said analysis device and said at least one position sensitive detector for storing either of said output or said result;

an interface device in electrical communication with said analysis device and said position sensitive detector for relaying commands from an operator to said analysis device, controlling said position detector, and displaying either of said output or said result; and at least one power source in electrical communication with said x-ray tube, at least one position sensitive detector, said analysis device, said storage device, and said interface device.

* * * * *